United States Patent [19]

Falk

[11] 4,222,269

[45] Sep. 16, 1980

[54] MOLTEN METAL SAMPLE LADLE WITH VENT TUBE

[76] Inventor: Richard Falk, 519 Westminster Dr., Waukesha, Wis. 53186

[21] Appl. No.: 32,436

[22] Filed: Apr. 23, 1979

[51] Int. Cl.³ .............................................. G01N 1/12
[52] U.S. Cl. ............................................ 73/425.4 R
[58] Field of Search ..................... 73/425.4 R, DIG. 9

[56] References Cited

U.S. PATENT DOCUMENTS

| | | | |
|---|---|---|---|
| 3,686,949 | 8/1972 | Hackett | 73/DIG. 9 |
| 4,046,016 | 9/1977 | Hackett | 73/425.4 R |
| 4,112,769 | 9/1978 | Falk | 73/425.4 R |

*Primary Examiner*—S. Clement Swisher
*Attorney, Agent, or Firm*—Henry C. Fuller

[57] ABSTRACT

A molten metal sampler includes opposed mold halves having recesses which form a fill passage and vent passage. The vent passage is positioned adjacent a supporting handle so that an elongated vent tube can be secured to the handle for support.

2 Claims, 3 Drawing Figures

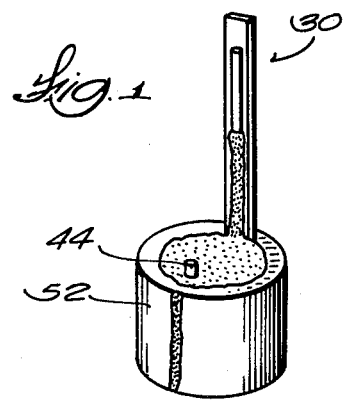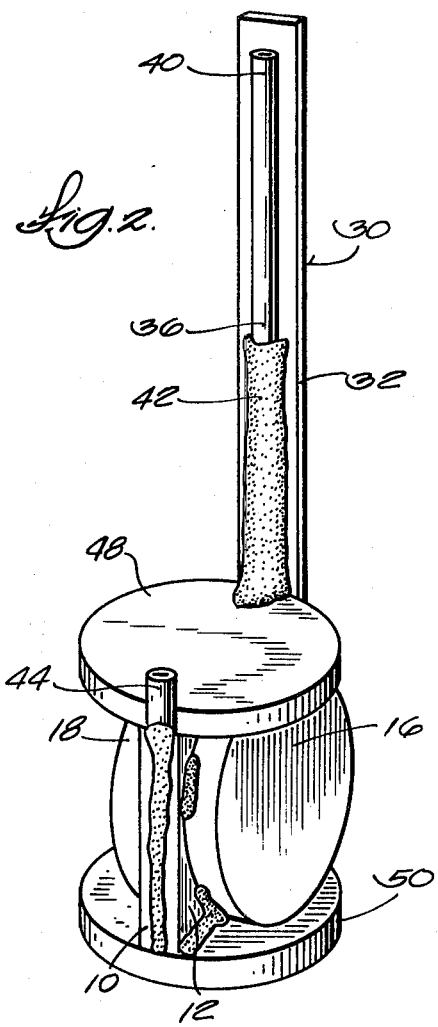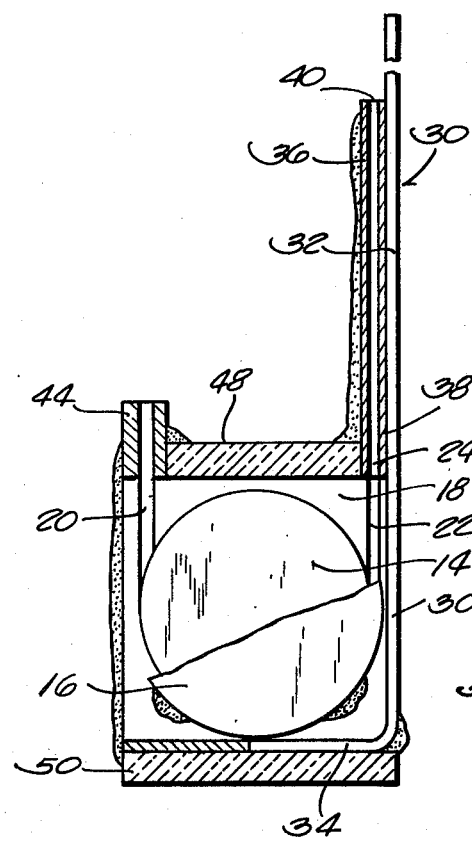

MOLTEN METAL SAMPLE LADLE WITH VENT TUBE

BACKGROUND OF THE INVENTION

The present invention relates to molten metal samplers, and more particularly to a ladle-type sampler which is intended to be used to dip samples from ingot molds and other slag-free melts. The invention is a further development of the subject matter of my U.S. Pat. No. 4,112,769.

SUMMARY OF THE INVENTION

The invention provides a dip sampler in which opposed mold halves are supported by a metal handle and in which the fill passage and the vent passage are located at the top of the assembly with a vent tube extending a substantial length along the handle, with the vent tube secured to the handle by refractory cement. The handle rigidifies and protects the fused quartz vent tube from breakage.

The mold halves are isolated from the melt by upper and lower fiberboard discs which are wrapped with a fiberglas jacket. The jacket is cemented to the fiberboard discs with refractory cement to form an integrated assembly.

Further objects, advantages and features of the invention will become apparent from the disclosure.

DESCRIPTION OF THE DRAWINGS

FIG. 1 is a perspective view of a sampler in accordance with the invention.

FIG. 2 is an enlarged perspective view of the sample mold without the protective jacket.

FIG. 3 is an enlarged sectional view of the integrated assembly shown in FIG. 2.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Referring to FIG. 2, the sampler includes opposed mold halves 10 and 12 which are square or rectangular in configuration and which have interior recesses or through openings 14 which are covered by ceramic discs 16 and 18 to form a mold cavity 15. Each of the mold halves 10 and 12 have recesses 20 to form a fill passage which communicates with the mold cavities. Each of the mold halves also has a recess 22 which form a vent passage 24 for escape of the air in the mold cavity to facilitate and promote filling of the sample cavity 15.

The mold halves are supported by a handle 30 which has a stem portion 32 and a base portion 34. The handle can be constructed from strip steel and desirably is slightly greater in width than the width of the assembled mold halves 10 and 12. The base portion 34 is at right angles with the portion 32 so that a corner is formed which interfits with the corner of the mold halves as illustrated in FIG. 3. A vent tube 36 is provided which has a lower end 38 registering with the vent passage 24 and an upper end 38 registering with the vent passage 24 and an upper end 40 remote from the sample cavity. The vent tube is secured to the handle by refractory cement 42. The vent tube 36 is sufficiently long so that it will be above the surface of the melt and facilitate entry of molten metal into the sample cavity. A fill tube 44 can also be provided with the fill tube 44 secured in registry with passage 20. The tube 44 is desirably made of steel or other metal to enhance filling of the mold cavity. The steel tube works far superior to a fused quartz or heat resistant glass tube, and this is believed to be due to capillary action.

The entire assembly is rigidified and the sample mold isolated from the melt by an assembly which includes an upper disc 48 and a lower disc 50 which are secured to the mold halves by refractory cement. The upper disc 48 has recesses to receive the vent tube and fill tube. The diameter of the discs 48 and 50 is approximately the same as the width of the mold halves. A split fiberglas or other protective sleeve 52 is wrapped around the periphery of the cardboard discs, as illustrated in FIG. 1, and the exposed faces of the fiberboard discs are completely coated with refractory cement to secure all of the parts together.

What is claimed is:

1. A molten metal sampler comprising opposed mold halves having a rectangular shape and opposed recesses defining a sample cavity, opposed recesses forming a fill passage and a vent passage along the upper edge of said mold halves, a handle having a bent portion at right angles with a stem portion and said sample mold having side and bottom edges respectively cemented to said stem portion and bent portion, upper and lower discs cemented to said top and bottom edges of said sample mold and an insulative jacket arranged around said discs and said handle to isolate said mold halves including a protective disc above said wall means defining the sample cavity, said fill tube extending through an opening in said disc and said vent tube extending through a second opening in said disc, and a protective shroud surrounding said wall means and interfitting with said protective discs.

2. A sampler in accordance with claim 1 wherein said fill tube is made of metal.